US008507756B2

(12) United States Patent
Roberts et al.

(10) Patent No.: US 8,507,756 B2
(45) Date of Patent: Aug. 13, 2013

(54) PLANT PROTECTION

(75) Inventors: Michael Richard Roberts, Lancaster (GB); Nigel Duncan Paul, Lancaster (GB); Jane Elizabeth Taylor, Lancaster (GB); Patricia Croft, North Yorkshire (GB); Jason Paul Moore, Leeds (GB)

(73) Assignee: Plant Bioscience Limited, Norwich, Norfolk (GB)

( * ) Notice: Subject to any disclaimer, the term of this patent is extended or adjusted under 35 U.S.C. 154(b) by 0 days.

(21) Appl. No.: 13/349,080

(22) Filed: Jan. 12, 2012

(65) Prior Publication Data

US 2012/0131700 A1    May 24, 2012

Related U.S. Application Data

(62) Division of application No. 12/373,646, filed as application No. PCT/GB2007/002611 on Jul. 12, 2007, now Pat. No. 8,115,053.

(51) Int. Cl.
 *A01H 9/00* (2006.01)
 *A01H 11/00* (2006.01)

(52) U.S. Cl.
 USPC ........................................................ 800/295

(58) Field of Classification Search
 USPC ........... 800/279, 283, 295; 514/2; 504/116.1
 See application file for complete search history.

(56) References Cited

U.S. PATENT DOCUMENTS

| | | | |
|---|---|---|---|
| 5,602,111 | A | 2/1997 | Misaki et al. |
| 5,776,860 | A | 7/1998 | Kamuro et al. |
| 6,114,284 | A | 9/2000 | Fujisawa et al. |
| 6,281,168 | B1 | 8/2001 | Shaner et al. |
| 2002/0035738 | A1* | 3/2002 | Thomma et al. ............... 800/279 |
| 2003/0162731 | A1 | 8/2003 | Dutcheshen |
| 2005/0260182 | A1 | 11/2005 | Strobel et al. |
| 2007/0142227 | A1 | 6/2007 | Rajamannan |
| 2007/0232494 | A1 | 10/2007 | Briand et al. |

FOREIGN PATENT DOCUMENTS

| | | |
|---|---|---|
| ES | 2129371 | 6/1999 |
| JP | 2003034607 | 2/2003 |
| RU | 2153794 | 8/2000 |
| WO | WO 98/24297 | 6/1998 |
| WO | WO 98/37752 | 9/1998 |
| WO | WO 98/56234 | 12/1998 |
| WO | WO 99/11133 | 3/1999 |
| WO | WO 01/30161 | 5/2001 |
| WO | WO 01/35747 | 5/2001 |
| WO | WO 01/58268 | 8/2001 |
| WO | WO 0/055480 | 7/2002 |
| WO | WO 02/055480 | 7/2002 |
| WO | WO 2005/018319 | 3/2005 |
| WO | WO 2005/074710 | 8/2005 |
| WO | WO 2005/094588 | 10/2005 |
| WO | WO 2007/074165 | 7/2007 |

OTHER PUBLICATIONS

Amruthesh, K.N. et al., "Unsaturated fatty acids from zoospores of *Sclerospora graminicola* induce resistance in pearl millet," Eur. J. Plant Path. (2005) 111:125-137 & Database CAPLUS accession No. 2005:102567.

Aver'Yanov, A.A. et al., "Blast resistance induced in rice by some Phthalocyanine metal complexes. Implication of active oxygen," Modern Fungicides and Antifungal Compounds II, International Reinhardsbrunn Symposium, 12th, Friedrichroda, Germany, May 24-29, 1998, pp. 389-395 & Database CAPLUS accession No. 1999:668780.

Buzi, A. et al., "Induction of resistance in melon to *Didymella bryoniae* and *Sclerotinia sclerotiorum* by seed treatments with acibenzolar-S-methyl and methyl jasmonate but not with salicylic acid," J. Phytopathology (2004) 152:34-42.

Canihos, Y., "Effect of herbicides on verticillium wilt of cotton and induction of phytoalexin gossypol production by host cells," Zeitschrift fur Pflanzenkrankheiten und Pflanzenschutz (Journal of Plant Disease and Protection) (1997) 104(5):516-522 & Database CAPLUS assession No. 1997:679816.

Gubanova, N.Y. et al., "Effects of polysaccharide elicitor on seed germination and resistance to diseases in beet plants," Fiziologiya I Biokhimiya Kul 'Turnykh Rastenii (2004) 36(6):478-484 (Database CAPLUS accession No. 2005:204648) abstract only.

Kirkpatrick, T.L. et al., "Greenhouse evaluation of experimental harpin-based seed and foliar treatments on root knot nematodes in cotton," 2006 Beltwide Cotton Conferences, San Antonio, Texas, Jan. 3-6, 2006, pp. 30-35 & Database CAPLUS accession No. 2006:1214317.

Latunde-Dada, A.O. et al., "The plant defence activator acibenzolar-S-methyl primes cowpea [*Vigna unguiculata* (L.) Walp.] seedlings for rapid induction of resistance," Physiol. Mol. Plant Path. (2001) 58:199-208 & Database CAPLUS accession No. 2001:512485.

Linden, J.C. et al., "Organic disease control elicitors," Agro-Food-Industry Hi-Tech (2000) 11(5):32-34 & Database CAPLUS accession No. 2000:880238.

Pena-Cortes, H. et al., "Involvement of jasmonic acid and derivatives in plant responses to pathogens and insects and in fruit ripening," J. Plant Growth Regul. (2005) 23:246-260.

Pozo, M.J. et al., "Jasmonates—signals in plant-microbe interactions," J. Plant Growth Regul. (2005) 23:211-222.

Rodriguez, A.T. et al., "Induction of defense response of *Oryza sativa* L. against *Pyriclaria grisea* (Cooke) Sacc. by treating seeds with chitosan and hydrolyzed chitosan," Pesticide Biochem. Phys. (2007) 89:206-215 & Database CAPLUS accession No. 2007:1073054.

(Continued)

*Primary Examiner* — Kent L Bell
(74) *Attorney, Agent, or Firm* — Andrus, Sceales, Starke & Sawall, LLP (57) ABSTRACT

The invention provides seed treatment compositions as well as their use, methods for treating seeds, methods of protecting plants against pests and also treated seeds and plants. In one embodiment there is provided a method of treating a seed with a seed treatment composition to induce a plant resistance mechanism against one or more pests in a plant grown from said seed.

5 Claims, 9 Drawing Sheets

(56) References Cited

OTHER PUBLICATIONS

Yakovleva, N.P., "Phytoalexins and their role in improving the health of plants," Trudy VSKhIZO (1973) 68:46-50—Database CAPLUS accession No. 1976:174967, Abstract only.

Zinov'Eva, S.V. et al., "Possibility of induction of plant resistance to nematodes by the elicitors of phytopathogenic fungi," Doklady Akademii Nauk (1996) 347(5):711-713—Database CAPLUS accession No. 1996:410188, Abstract only.

International Search Report and Written Opinion for Application No. PCT/GB2007/002611 dated Jul. 30, 2008 (16 pages).

Restriction Requirement for U.S. Appl. No. 12/373,646 dated Sep. 9, 2010 (9 pages).

Office Action for U.S. Appl. No. 12/373,646 dated Mar. 16, 2011 (8 pages).

Aver'Yanov, A.A. et al., "Blast resistance induced in rice by some Phthalocyanine metal complexes. Implication of active oxygen," Modern Fungicides and Antifungal Compounds II, International Reinhardsbrunn Symposium, 12th, Friedrichroda, Germany, May 24-29, 1998, pp. 389-395 & Database CAPLUS accession No. 1999:668780.

Canihos, Y., "Effect of herbicides on verticillium wilt of cotton and induction of phytoalexin gossypol production by host cells," Zeitschrift fur Pflanzenkrankheiten and Pflanzenschutz (Journal of Plant Disease and Protection) (1997) 104(5):516-522 & Database CAPLUS accession No. 1997:679816.

Gubanova, N. Y. et al., "Effects of polysaccharide elicitor on seed germination and resistance to diseases in beet plants," Fiziologiya I Biokhimiya Kul 'Turnykh Rastenii (2004) 36(6):478-484 (Database CAPLUS accession No. 2005:204648) abstract only.

Rodriguez, A.T. et al., "Induction of defense response of *Oryza sativa* L. against *Pyricularia grisea* (Cooke) Sacc. By treating seeds with chitosan and hydrolyzed chitosan," Pesticide Biochem. Phys. (2007) 89:206-215 & Database CAPLUS accession No. 2007:1073054.

Yakovleva, N.P., "Phytoalexins and their role in improving the health of the plants," Trudy VSKhIZO (1973) 68:46-50—Database CAPLUS accession No. 1976:174967, Abstract only.

\* cited by examiner

PLANT PROTECTION

CROSS-REFERENCE TO RELATED APPLICATIONS

This patent application is a division of U.S. National application Ser. No. 12/373,646, filed on Mar. 3, 2009, which is, a national stage filing under 35 U.S.C. 371 of International Application No. PCT/GB2007/002611, filed on Jul. 12, 2007, which claims foreign priority benefits to United Kingdom Patent Application No. 0613901.8, filed on Jul. 13, 2006. These applications are incorporated herein by reference in their entireties.

FIELD OF INVENTION

The present invention relates to plant protection, in particular to seed treatment compositions and their use, to methods for treating seeds, to methods of protecting plants against pests and to seeds and plants.

BACKGROUND TO THE INVENTION

Crop diseases are caused by plant pathogenic micro-organisms, (e.g. fungi, bacteria or viruses) which can infect the plant at various stages of development, from the dormant seed to the mature plant. Attack by different pathogens results in widely different diseases, from rapid and large-scale tissue death to long-term chronic infections. Crop pests encompass a wide range of animals, but most are invertebrates including nematodes and arthropods such as insects or mites. These pests feed on plant tissues, with different pests attacking different tissues in different ways. For example, at one extreme nematodes may suck the contents of individual root cells while large insect pests may chew away large areas of foliage.

Leaving aside cultivation practices such as crop rotation and sanitation, much of crop protection has relied on the application of agents (pesticides, which is the term used for agents used against both pests and diseases) that are directly toxic to the pest or disease-causing microbe. For example, pests may be treated using insecticides or nematicides, diseases treated with anti-microbial agents such as fungicides or bactericides. Depending on the site of infection or attack, pesticides may be applied to the crop in a number of ways, including foliar sprays, soil drenches or seed treatments. Regardless of application method, conventional pesticides may act through direct contact with the pest or pathogen, or may be absorbed by the plant and fulfil its function when plant tissues are consumed (e.g. systemic pesticides).

When known pesticides are used as seed treatments the seeds are coated with agents that are designed to inhibit or interfere directly with pathogens or pests and these are dried onto the seeds. Such treatments are mostly aimed at providing direct protection against soil borne pathogens or pests that attack the seed, seedling or roots. In most cases, the observed protection is transient and declines as the protectant is degraded, diluted or localised in the soil and roots as growth progresses.

A disadvantage of known pesticides is that many are also toxic to non-target species, resulting in reductions in biodiversity and even harming beneficial species such as pollinating or predatory insects. In addition there are consumer concerns related to the possible human toxicity of some known pesticides.

Genetic modification has been used as an alternative to pesticides as has Integrated Pest Management (IPM), which combines cultivation practices with the use of pest parasites or predators as a means of biological control. However, each has disadvantages.

A further approach to pest control attempts to make use of plants natural defence systems. Plants respond to a vast range of environmental stimuli. Responses include those that provide protection against pests (e.g. herbivores such as insects) and pathogens (e.g. fungi, bacteria, viruses etc). Plant responses to pest or pathogen attack are brought about by a chain of events that link the initial recognition of the stimulus to changes in cells of the plant that ultimately lead to protection. Thus, in response to wounding and to pest/pathogen challenge, there are local and systemic events induced, with signal transduction pathways occurring at the local site, systemic signal(s) communicating the local events around the plant, and signal transduction pathways occurring in distant cells that are responding to the systemic signal(s).

Plant signalling molecules play a central role in these induced responses to environmental stimuli, since they act as the intermediate molecular signals which link attack to the internal end-effect(s) within the plant. For example, in a variety of plant species, jasmonic acid is known to accumulate transiently following wounding or herbivore attack, and is linked to activation of wound-responsive genes. Another example is during the interactions of plants with pathogens, when salicylic acid is known to increase in quantity and is considered to be a central regulator of local and systemic acquired resistance (SAR) and the activation of defence-related genes associated with disease resistance.

Jasmonic acid (JA) has been applied as an external foliar spray (and also as a root drench) to induce insect-pest resistance in crops such as tomato (*Solanum lycopersicum*) and grapevine. However, such foliar (and root) applications of JA or its derivatives are prone to cause direct damage to the crop, by causing phytotoxicity for example, and are too expensive to be viable commercially.

U.S. Pat. No. 5,977,060 discloses the use of the Harpin protein of *Erwinia amylovora* to induce hypersensitive and systemic acquired resistance responses in crops to provide disease protection against viruses as well as protection against soil borne fungi, nematodes and some insects attacking early seedling growth. However, protection provided against insects by a seed soak appears limited to aphids, i.e. sap feeding arthropods. The soak is applied prior to sowing and it appears the plant protection would actually be provided by carry over of the seed soak onto seedlings, effectively applying the protein directly to the seedlings. Harpin also has the disadvantage that it is the result of genetic manipulation which may greatly limit its use in many areas.

The use of jasmonic acid as a seed soak applied to germinating bean and melon seeds is known but only for the purpose of providing protection against fungal disease. The protection afforded to plants was limited and likely to have arisen from the jasmonic acid transferring, directly onto germinating seedlings.

WO02055480 relates to the application of coronalon and related compounds in inducing resistance to pathogens including insects. Coronalon is an artificial (chemically synthesised) analogue of coronatine which is an analogue of JA-amino acid conjugates, and which has similar, though not identical, biological activity to JA. However, the coronalon was applied to growing plants and thus this disclosure is little different to a JA foliar spray.

WO0141568 discloses the use of Cis-Jasmone sprays to induce plant volatile emissions that repel insect pests and attract beneficial insects. Again, this is applied directly to growing plants.

Accordingly, the present invention aims to address at least one disadvantage associated with the prior art whether discussed herein or otherwise.

SUMMARY OF INVENTION

According to a first aspect of the present invention there is provided a method of treating a seed with a seed treatment composition to induce a plant resistance mechanism against one or more pests in a plant grown from said seed so as to restrict plant damage by pests, the method comprising applying the treatment composition to a seed.

Preferably, the method comprises applying the treatment composition to a non germinated seed. Suitably, the method comprises applying the treatment composition to a non germinating seed capable of subsequent germination. Alternatively, the method may comprise applying the treatment composition to a germinating seed.

As used herein the term "pests" excludes "disease". Specifically excluded from the term "pests" are pathogens which include fungi, bacteria and viruses. Included in the term "pests" are invertebrates including nematodes, molluscs and arthropods such as insects and mites.

Suitably, the pests comprise herbivorous pests. Suitably, the pests comprise herbivorous invertebrates. The pests may comprise nematodes and/or molluscs and/or herbivorous arthropods. Alternatively, or in addition, the pests may comprise vertebrates such as rabbits. The pests may comprise pests which feed on foliage. The pests may comprise pests which feed on sap. The induced plant resistance mechanism may thus act to restrict plant damage by sap and/or foliage eating pests. Alternatively, or in addition the pests may comprise pests which feed on other plant parts and the induced plant resistance mechanism may act against such pests. The method/treatment composition may provide protection against disease, including pathogens such as fungi, bacteria and viruses, as well as against pests.

As used herein the term "seed treatment composition" includes seed coating and seed soak compositions.

Suitably, the seed treatment composition comprises a seed soak. The method may thus comprise a method of treating a seed by soaking it in seed treatment composition.

Suitably, the treatment composition comprises a treatment agent (suitably a plant signalling chemical) selected from jasmonic acid (JA) or related members of the jasmonate family of oxylipins, or other compounds that activate JA-dependant herbivore resistance pathways including: jasmonic acid or its jasmonate salts, such as, for example, potassium or sodium jasmonate; jasmonic acid methyl ester ('methyl jasmonate'); jasmonic acid-L-amino acid (amide-linked) conjugates, such as, for example, the conjugate with L-isoleucine or the conjugates with L-valine, L-leucine and L-phenylalanine; 12-oxo-phytodienoic acid; coronatine (an amide of coronafacic acid with 2-ethyl-1-aminocyclopropane carboxylic acid); coronafacoyl-L-serine and coronafacoyl-L-threonine; methyl esters of 1-oxo-indanoyl-isoleucine and 1-oxo-indanoyl-leucine; coronalon (2-[(6-ethyl-1-oxo-indane-4-carbonyl)-amino]-3-methyl-pentanoic acid methyl ester); or combinations thereof.

Suitably, the treatment composition comprises a treatment agent selected from the group consisting of: jasmonic acid or its jasmonate salts, such as, for example, potassium or sodium jasmonate; jasmonic acid methyl ester ('methyl jasmonate'); jasmonic acid-L-amino acid (amide-linked) conjugates, such as, for example, the conjugate with L-isoleucine or the conjugates with L-valine, L-leucine and L-phenylalanine; 12-oxo-phytodienoic acid; coronatine (an amide of coronafacic acid with 2-ethyl-1-aminocyclopropane carboxylic acid); coronafacoyl-L-serine and coronafacoyl-L-threonine; methyl esters of 1-oxo-indanoyl-isoleucine and 1-oxo-indanoyl-leucine; coronalon (2-[(6-ethyl-1-oxo-indane-4-carbonyl)-amino]-3-methyl-pentanoic acid methyl ester); or combinations thereof.

Suitably, the treatment composition comprises a single treatment agent selected from the group consisting of: jasmonic acid or its jasmonate salts, such as, for example, potassium or sodium jasmonate; jasmonic acid methyl ester ('methyl jasmonate'); jasmonic acid-L-amino acid (amide-linked) conjugates, such as, for example, the conjugate with L-isoleucine or the conjugates with L-valine, L-leucine and L-phenylalanine; 12-oxo-phytodienoic acid; coronatine (an amide of coronafacic acid with 2-ethyl-1-aminocyclopropane carboxylic acid); coronafacoyl-L-serine and coronafacoyl-L-threonine; methyl esters of 1-oxo-indanoyl-isoleucine and 1-oxo-indanoyl-leucine; and coronalon (2-[(6-ethyl-1-oxo-indane-4-carbonyl)-amino]-3-methyl-pentanoic acid methyl ester).

Suitably, the treatment composition comprises jasmonic acid (JA) as a treatment agent. Suitably, the treatment composition comprises jasmonic acid (JA) as the sole treatment agent.

Suitably, the treatment composition comprises methyl jasmonate (MeJA) as a treatment agent. The treatment composition may comprise methyl jasmonate (MeJA) as the sole treatment agent.

It is believed that jasmonic acid (JA) is a ubiquitous regulator of the responses to herbivore attack in plants. It is understood to form part of a long distance plant defence signalling pathway and when applied exogenously (to foliar tissues or roots) may induce defence related responses to arthropod and other pests for the purpose of reducing the damage done at the time of attack and likelihood of future attack. The octadeconoid pathway leading to JA biosynthesis is understood to be linked to the activation of plant defence responses.

However, given the current understanding of induced plant defences against pest attack, it would not be expected that applying compounds inducing defence systems to the seed would protect the growing plant from pest attack over an extended period. The transition from seed to growing plant involves major metabolic re-programming and the production of tissues not present in the seed, even in a meristematic form. Despite this, jasmonic acid mediated defence responses against herbivorous insects which may be induced by the present invention may be surprisingly effective. Also surprisingly, subsequent germination of treated seeds may be substantially uninhibited by the treatment method.

Surprisingly, it has been found by the present inventors that applying a treatment composition to seeds may induce elements of natural defences that target pests in plants germinated from treated seeds. This may continue to be the case a considerable time after germination which is not at all expected. This may be so even when a treatment agent is applied at low concentrations to seed and may result in persistent pest control over many weeks, long after the active compound has been naturally degraded. Unexpectedly, it has been found that when applied to non-germinated seed protection may be induced in the subsequent growing plant.

Suitably, resistance against pests is caused by a defence mechanism that is regulated by the oxylipin pathway (also known as the jasmonate pathway or octadecanoid pathway).

Suitably, the seed treatment composition comprises an aqueous composition. The treatment composition may comprise a non-aqueous solvent, suitably an alcohol, for example ethanol.

Suitably, the treatment composition comprises treatment agent, for example jasmonic acid, at a concentration of at least 10 μM, for example of 1 mM or more. The treatment composition may comprise treatment agent, for example jasmonic acid, at a concentration of between 10 μM, and 50 mM, suitably of between 0.1 mM and 15 mM, for example of between 1 mM and 5 mM. The treatment composition may comprise treatment agent in an amount of up to 10 mM.

The treatment composition may comprise treatment agent in an amount of at least 0.1 mM, for example at least: 0.5 mM; 1.0 mM; 1.5 mM; 2.0 mM; 2.5 mM; 3.0 mM; 3.5 mM; 4.0 mM; 4.5 mM; 5.0 mM; 6.0 mM; 7.0 mM; 8.0 mM; 9.0 mM; or 10 mM.

The treatment composition may comprise treatment agent in an amount of no greater than 15 mM, for example no greater than: 14 mM, 13 mM, 12.5 mM, 12.0 mM, 11.5 mM, 11.0 mM, 10.5 mM, 10.0 mM, 9.5 mM, 9.0 mM, 8.0 mM, 7.0 mM or 6.0 mM.

The treatment composition may comprise a non aqueous solvent, suitably an alcohol, in a concentration of at least 1 mM. The treatment composition may comprise a non aqueous solvent, suitably an alcohol, in a concentration of between 1 mM and 100 mM, suitably between 10 mM and 100 mM, for example between 30 mM and 50 mM.

Suitably, the treatment composition comprises water and treatment agent and suitably also a non-aqueous solvent, suitably alcohol. Suitably, at least 95% by weight, for example at least 99% by weight of the treatment composition may consist of water, treatment agent and alcohol. Suitably, the treatment composition consists of water, treatment agent and alcohol. The treatment composition may consist of water, ethanol and jasmonic acid.

Suitably, the method comprises applying seed treatment composition to a non germinated seed which may be a dormant seed.

Suitably, the method comprises applying a seed treatment composition to a seed under conditions which hinder germination. The seed treatment composition may be applied to a seed under conditions of low temperature and/or darkness.

Suitably, the seed treatment composition is applied to a seed at a temperature of 10° C. or less, for example: 9° C., 8° C., 7° C., 6° C., 5° C. or 4° C. or less. Suitably, the seed is retained at such a temperature throughout the treatment process.

Suitably, the method comprises maintaining a seed in a non germinating state during treatment by use of cold temperatures, suitably of less than 10° C. but greater than the freezing point of the treatment composition.

Suitably, the method comprises placing a seed in contact with a seed treatment composition for a period of 1 hour or more, suitably for a period of at least 6 hours, for example at least 12 hours. Suitably, the method comprises placing a seed in contact with a seed treatment composition for between 1 hour and 72 hours, suitably, for between 6 hours and 48 hours, for example around 24 hours.

Suitably, the treatment composition comprises a liquid applied to the seed, for example a seed soak. Suitably, the treatment composition comprises jasmonic acid applied as a liquid.

Alternatively, the treatment composition may be applied as a dust, powder, slurry or vapour. The treatment agent may for example comprise methyl jasmonate applied as a vapour.

If applied as a powder the treatment composition may comprise a sticking agent. If applied; as a slurry the slurry may comprise either a wettable powder, water dispersible powder or a micro encapsulation/capsule suspensions. If applied as a liquid then a concentrate may require dilution before application to the seed. Jasmonic acid or jasmonate derived seed coatings may for example be readily applied as a liquid, but could also be applied as a dust or slurry if sufficiently diluted with a filler such as clay to avoid over application.

To coat seeds with a treatment composition the composition may be mechanically blended with the seeds to ensure uniform coverage and any moisture may be encouraged to evaporate to avoid triggering premature germination. Variants of the coating process may involve applying several different treatments to the seed at the same time via a formulation (where these treatments are compatible as regards their means of application) or applying several different treatments consecutively to build up a series of treatment layers in a process known as pelleting. One of several well known polymer or other coatings may be applied to seal the seed against dusting off and if required to also colour the seed for identification.

Suitably, the method comprises soaking a seed by partially or fully, most suitably fully, immersing, a seed in a treatment composition. Suitably, the method comprises immersing a seed in a treatment, composition such that the seed is placed in contact with the composition for a period of at least 1 hour as detailed above.

Suitably, the method comprises drying a seed subsequent to the application of the treatment composition to the seed. The method may comprise allowing the seed to dry naturally. Alternatively, the method may comprise applying heat to dry the seed. Suitably, drying the seed subsequent to application of treatment composition and prior to germination does not hinder the induction of plant resistance mechanisms.

The method may comprise washing a seed subsequent to the application of the treatment composition to the seed. The method may comprise washing the seed with water. The method may comprise partially or fully, most suitably fully, immersing the seed in water. The method may comprise washing the seed between the step of applying the treatment composition to the seed and a step of drying the seed. Suitably, washing the seed subsequent to application of treatment composition and prior to germination does not hinder the induction of plant resistance mechanisms.

Suitably, a seed treated by the method can be stored for at least 24 hours prior to being sown. Suitably, a seed treated by the method can be stored in substantially the same manner as an untreated seed prior to use. A treated seed may be stored for at least 24 hours prior to germination being initiated, suitably at least 72 hours, for example a week or more. A treated seed may for example be stored for a month or more prior to being sown and germination initiated. Suitably, storing the seed subsequent to application of treatment composition and prior to germination does not hinder the induction of plant resistance mechanisms. A treated seed may thus be stored for a week or more prior to germination being initiated without hindering the induction of plant resistance mechanisms.

Suitably, a seed treated by the method is of a monocotyledonous or dicotyledonous plant. Suitably, a seed treated by the method is of a horticultural or agricultural crop. The crop may be a crop grown for commercial purposes.

Suitably, the method comprises applying a treatment composition such that resistance against pests in a plant grown from a treated seed is caused by defence mechanisms that are regulated by the oxylipin pathway (also known as the jasmonate pathway or octadecanoid pathway).

Suitably, the resistance mechanism is induced due to the treatment of the seed. Suitably, resistance against pests is not induced solely by carry over of the composition onto a plant germinated from the treated seed. The resistance mechanism may be induced due to the treatment of the seed rather than due to carry over of treatment composition from the seed onto a germinating plant.

Suitably, a plant germinated from a seed treated according to the method may exhibit resistance to pest damage at least 1 week after germination, suitably at least 2 weeks, for example; 3; 4; 5; 6; 7 or 8 weeks or more after germination.

Suitably, a plant germinated from a seed treated according to the method may exhibit greater resistance to pest damage than an otherwise equivalent plant germinated from an untreated seed at least 1 week after germination, suitably at least 2 weeks, for example; 3; 4; 5; 6; 7 or 8 weeks or more after germination.

Suitably, a pest resistance mechanism in a plant germinated from a seed treated according to the method may act by reducing survival of a pest and/or reducing plant damage by a pest and/or reducing reproduction of a pest.

The seed treatment composition may induce a plant resistance mechanism against one or more pests in a plant grown from said seed which restricts pest survival and/or pest numbers and/or pest growth and/or pest reproduction.

Suitably, a plant located within the proximity of a plant germinated from a seed treated according to the method may also be at reduced risk from plant damage by pests. Suitably, production of plant volatile signalling compounds produced by a plant from a seed treated by the method may provide resistance against pest damage in nearby untreated plants.

Suitably, there are no problems associated with phytotoxicity in plants germinated from treated seeds.

Suitably, there are no problems associated with germination of treated seeds.

Suitably, the method of treatment substantially avoids causing detrimental effects on plants, or the yield or quality of produce the plant is grown to produce, grown from the treated seed. Suitably, the method is such that phytotoxicity in a plant grown from a treated seed is substantially avoided.

The method may comprise treating a seed with a composition according to the third aspect as described hereafter.

According to a second aspect of the present invention there is provided a seed from which a plant resistant to pest damage can be grown, wherein the seed comprises a seed treated with a seed treatment composition to induce a plant resistance mechanism against one or more pests in a plant grown from said seed so as to restrict plant damage by pests.

Preferably, the seed comprises a non germinated seed. Suitably, the seed comprises a non germinating seed capable of subsequent germination.

Suitably, the seed comprises a seed treated according to the method of the first aspect. The seed may comprise a seed treated with a composition according to the third aspect as described hereafter.

Suitably, the seed comprises any feature as described in relation to the first aspect.

The plant may comprise any feature as described in relation to the first aspect. The pest may comprise any feature as described in relation to the first aspect. The seed treatment composition may comprise any feature as described in relation to the first aspect. The plant resistance mechanism may comprise any feature as described in relation to the first aspect.

According to a third aspect of the present invention there is provided a seed treatment composition for treating a seed to induce a plant resistance mechanism against one or more pests in a plant grown from said treated seed so as to restrict plant damage by pests.

Suitably, the treatment composition is arranged to be employed in a method according to the first aspect.

Suitably, the treatment composition comprises a treatment agent selected from jasmonic acid (JA) or related members of the jasmonate family of oxylipins, or other compounds that activate JA-dependant herbivore resistance pathways including: jasmonic acid or its jasmonate salts, such as, for example, potassium or sodium jasmonate; jasmonic acid methyl ester ('methyl jasmonate'); jasmonic acid-L-amino acid (amide-linked) conjugates, such as, for example, the conjugate with L-isoleucine or the conjugates with L-valine, L-leucine and L-phenylalanine; 12-oxo-phytodienoic acid; coronatine (an amide of coronafacic acid with 2-ethyl-1-aminocyclopropane carboxylic acid); coronafacoyl-L-serine and coronafacoyl-L-threonine; methyl esters of 1-oxo-indanoyl-isoleucine and 1-oxo-indanoyl-leucine; coronalon (2-[(6-ethyl-1-oxo-indane-4-carbonyl)-amino]-3-methyl-pentanoic acid methyl ester); or combinations thereof.

Suitably, the treatment composition comprises a treatment agent selected from the group consisting of: jasmonic acid or its jasmonate salts, such as, for example, potassium or sodium jasmonate; jasmonic acid methyl ester ('methyl jasmonate'); jasmonic acid-L-amino acid (amide-linked) conjugates, such as, for example, the conjugate with L-isoleucine or the conjugates with L-valine, L-leucine and L-phenylalanine; 12-oxo-phytodienoic acid; coronatine (an amide of coronafacic acid with 2-ethyl-1-aminocyclopropane carboxylic acid); coronafacoyl-L-serine and coronafacoyl-L-threonine; methyl esters of 1-oxo-indanoyl-isoleucine and 1-oxo-indanoyl-leucine; coronalon (2-[(6-ethyl-1-oxo-indane-4-carbonyl)-amino]-3-methyl-pentanoic acid methyl ester); or combinations thereof.

Suitably, the treatment composition comprises jasmonic acid (JA) as a treatment agent.

Suitably, the treatment composition comprises an aqueous composition. The treatment composition may comprise a non-aqueous solvent, suitably an alcohol, for example ethanol.

Suitably, the treatment composition comprises water and treatment agent and suitably also a non-aqueous solvent, suitably alcohol. Suitably, the treatment composition essentially consists of water, treatment agent and non aqueous solvent. Suitably, the treatment composition essentially consists of water, treatment agent and alcohol.

Suitably, the treatment composition comprises any feature as described in relation to the first aspect.

The seed may comprise any feature as described in relation to the first aspect. The seed may be a non germinating seed. The plant may comprise any feature as described in relation to the first aspect. The pest may comprise any feature as described in relation to the first aspect. The plant resistance mechanism may comprise any feature as described in relation to the first aspect.

According to a fourth aspect of the present invention there is provided a method of providing a plant with resistance to pest damage, the method comprising applying a seed treatment composition to a seed and subsequently growing a plant from said seed, wherein the treatment composition induces a plant resistance mechanism against one or more pests in said plant grown from said treated seed so as to restrict plant damage by pests.

Suitably, said plant comprises greater resistance to pests than an otherwise equivalent plant grown from untreated seed.

Preferably, the method comprises applying the treatment composition to a non germinated seed. Suitably, the method comprises applying the treatment composition to a non germinating seed capable of subsequent germination. Alternatively, the method may comprise applying the treatment composition to a germinating seed.

Suitably, the method comprises treating a seed according to the method of the first aspect. The method may employ a seed according to the second aspect. The method may employ a treatment composition according to the third aspect.

The method may comprise treating a seed with a treatment composition and subsequently washing and/or drying and/or storing said seed prior to germination.

Subsequent to treatment, which may include washing and/or drying, the method may comprise handling, which may include storing, the treated seed in substantially the same manner as known untreated seed.

Suitably, the plant comprises any feature as described in relation to the first aspect.

Suitably, the plant prepared by the method exhibits resistance against pests caused by defence mechanisms which are regulated by the oxylipin pathway which may also be referred to as the jasmonate pathway or octadecanoid pathway.

The seed may comprise any feature as described in relation to the first aspect. The peat may comprise any feature as described in relation to the first aspect. The seed treatment composition may comprise any feature as described in relation to the first aspect. The plant resistance mechanism may comprise any feature as described in relation to the first aspect.

According to a fifth aspect of the present invention there is provided a plant resistant to pest damage, wherein the plant comprises a plant provided by a method according to the fourth aspect and/or grown from a seed according to the second aspect and/or grown from a seed treated according to the method of the first aspect and/or grown from a seed treated with a composition according to the third aspect.

The fifth aspect may employ any feature as described in relation to the first, second, third or fourth aspects.

According to a sixth aspect of the present invention there is provided a method of restricting pest damage to a plant, the method comprising locating said plant in proximity to a plant according to the fifth aspect.

The sixth aspect may employ any feature as described in relation to the first, second, third or fourth aspects.

According to a seventh aspect of the present invention there is provided the use of a seed treatment composition to treat a seed in order to induce a plant resistance mechanism against one or more pests in a plant grown from said seed so as to restrict plant damage by pests.

Suitably, the seed treatment composition comprises a composition according to the third aspect.

Suitably, the resistance against pests is caused by a defence mechanism that is regulated by the oxylipin pathway (also known as the jasmonate pathway or octadecanoid pathway).

The seventh aspect may employ any feature as described in relation to the first, second, third or fourth aspects.

According to an eighth aspect of the present invention there is provided the use of a seed treatment composition to treat a seed in order to induce a plant resistance mechanism against one or more pests in a plant grown from said seed in order to restrict pest survival and/or pest numbers and/or pest growth and/or pest reproduction.

Suitably, the treatment composition comprises a composition according to the third aspect.

Suitably, the resistance against pests is caused by a defence mechanism that is regulated by the oxylipin pathway (also known as the jasmonate pathway or octadecanoid pathway).

The eighth aspect may employ any feature as described in relation to the first, second, third or fourth aspects except where such features are mutually exclusive.

BRIEF DESCRIPTION OF THE DRAWINGS

The present invention will now be illustrated by way of example with reference to the accompanying drawings in which.

DETAILED DESCRIPTION OF THE INVENTION

Preparation of Jasmonic Acid (JA) and Methyl Jasmonate (MeJA) Solutions.

Jasmonic acid (JA) and Methyl Jasmonate (MeJA) solutions were prepared immediately prior to treatment of seeds.

To prepare the Jasmonic acid solution 250 mg of JA was dissolved in 1 ml of ethanol and made up to a volume of 400 ml with deionised water to give a solution of 3 mM JA in 42.8 mM Ethanol as follows:

1. The mass of Jasmonic acid in a 250 mg vial of JA (Sigma-Aldrich) was recorded from the vial's label.
2. The label was removed and acetone used to also remove any glue from the outside of the vial.
3. After allowing the vial to dry for 5 minutes it was weighed to the nearest mg.
4. A 500 mL volumetric flask was filled with deionised water up to the line.
5. 5 ml of water was removed from the volumetric flask using a 1000 µl Gilson pipette and then a further 100 ml using an analytical 100 ml pipette.

6. 1 ml of ethanol was added to the vial of JA using a 1000 μl Gilson pipette, the lid of the vial replaced and the vial shaken to dissolve the JA. The use of ethanol is necessary as JA will not dissolve in water directly.

7. The contents of the vial were then transferred to the 500 ml volumetric flask using a 1000 ul Gilson pipette.

8. 1 mL of deionised water was added to the empty vial using a 1000 ul Gilson pipette, the lid of the vial replaced and the vial again shaken vigorously.

9. The contents of the vial were then transferred to the 500 ml volumetric flask using a 1000 ul Gilson pipette.

10. Steps 8 and 9 were repeated a further 3 times.

11. The volumetric flask (now containing 400 ml of liquid and 250 mg of JA) was stoppered and shaken vigorously.

12. The vial was dried to constant weight in a 150° C. oven and its weight recorded.

13. The concentration of JA in the volumetric flask was calculated from the weight difference between the two weighings of the vial.

A 1.5 mM JA solution was prepared by diluting the 3 mM JA solution 2 fold with deionised water containing 42.8 mM ethanol. A variety of other concentrations were prepared for Example 9 according to the method above with quantities modified appropriately.

A 3.0 mM MeJA solution was prepared using substantially the same method as described above but using MeJA in place of JA. To produce the MeJA solution 269 mg of MeJA was dissolved in 1 ml of ethanol and made up to a volume of 400 ml with deionised water to give a solution of 3 mM MeJA in 42.8 mM Ethanol.

Seed Treatment—Overview

Tomato, pepper, maize and wheat seeds were treated with 3 mM JA or 1.5 mM JA solutions or with 3 mM methyl jasmonate (MeJA) or with deionised water containing 42.8 mM ethanol (control) by full submersion of up to 40 seeds in a Petri dish of solution wrapped in foil for a period of 24 hours at 4° C. in a fridge. A temperature of 4° C. was used both to prevent degradation of the jasmonic acid solutions and to prevent germination of the seeds.

The seeds were then removed from the treatment solution and washed in 1 liter of deionised water for 5 minutes to remove the JA or MeJA coating the outside of the seeds.

Growth and Challenge of Tomato, Pepper, Maize and Wheat Plants—Overview

Tomato seeds were sown in rockwool blocks and grown on peat-based compost in glass houses at 12° C.-28° C. under artificial light on a 16 hour light and 8 hour dark cycle for 48, 56 or 70 days.

Pepper seeds were sown in peat-based compost and grown in unheated glass houses under ambient conditions in the summer.

Wheat and maize seeds were sown in peat-based compost and grown in unheated glass houses with supplementary lighting. (600 W SON-T lamps, for 16 hours per day) in the autumn.

Tomato plants were then challenged with *Tetranychus urticae* (two-spotted spider mite) which were allowed to feed for 9 days, *Manduca sexta* (tobacco hornworm) caterpillars which were allowed to feed for 4 days or *Myzus persicae* (aphid), which were allowed to feed for 10 or 12 days. In each case these organisms were restricted to the plant on which they had originally been placed. Pepper plants were challenged with *Myzus persicae* (aphid), which were allowed to feed for 2 weeks. Maize and wheat plants were challenged with *Spodoptera exempta* caterpillars which were allowed to feed for 2 days (maize) or 3 days (wheat).

The effect of *Tetranychus urticae* on plants was measured by means of counting the number of live and dead mites on each plant and the number of mite eggs present using a dissecting microscope.

The effect of *Myzus persicae* on plants was determined by counting the aphid population on each plant under a dissecting microscope at ×10 magnification.

The effect of *Manduca sexta* or *Spodoptera exempta* on plants was determined by measurement of the leaf area eaten, measured using a leaf area meter.

EXAMPLE 1

Seeds of a UK commercial F1 hybrid tomato variety (cv. Carousel) were treated with either 1.5 or 3.0 mM jasmonic acid (JA) and 42.8 mM ethanol in deionised $H_2O$ for a period of 24 hours at 4° C. in the dark. Those seeds were then removed from solution and washed in deionised $H_2O$ only to remove the JA coating the outside of the seed. Those seed were then germinated in a commercial manner using rockwool blocks and were grown on under glasshouse conditions appropriate to this crop. Plants were challenged with two-spotted spider mite (*Tetranychus urticae*) 7 weeks after treatment a common crop pest, acting here as a "model herbivore".

Figure 1:
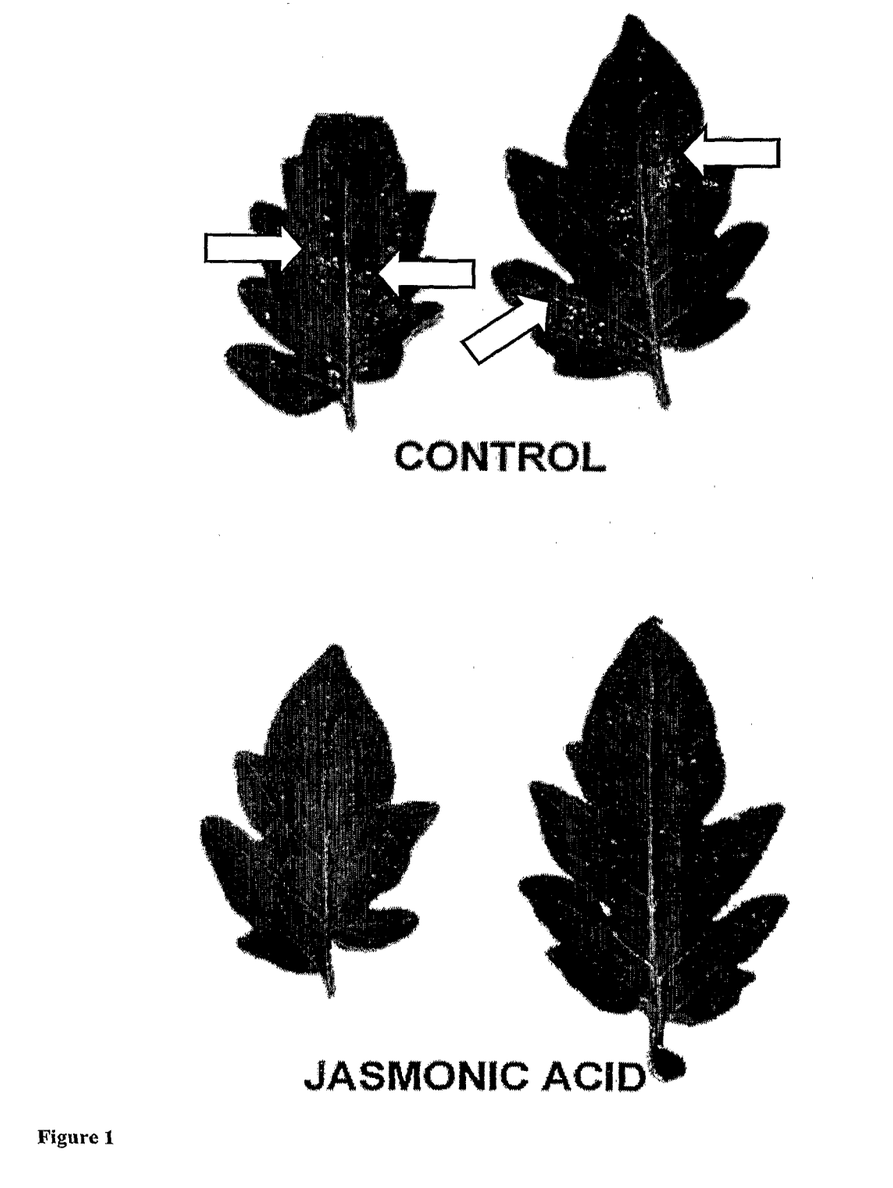
FIG. 1. shows the effects of JA seed treatments on spider mite damage to tomato plants.

Visual damage caused by red spider mite attack (the characteristic pale stippling of the leaf surface due to the pest feeding activity) was substantially reduced (FIG. 1—Control and 3.0 mM JA only). The observed resistance induced was significant even 8 weeks after application of the JA to the seeds.

Figure 2:
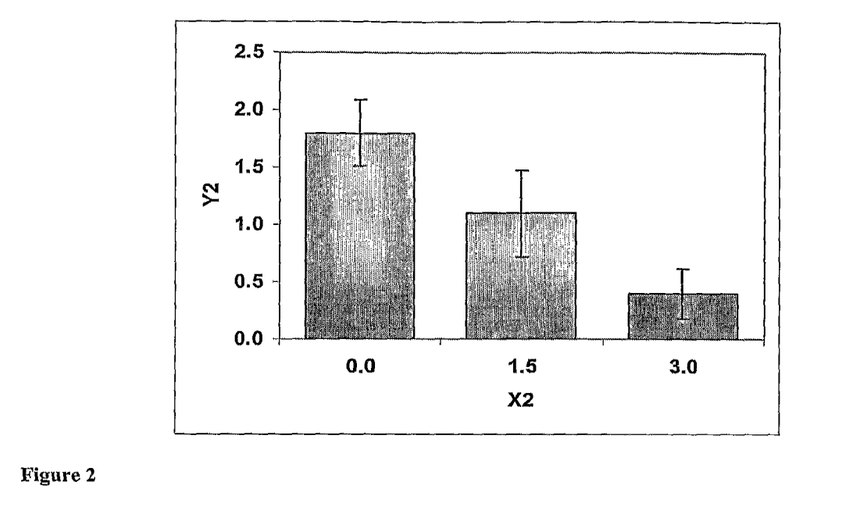
FIG. 2. shows the effects of JA seed treatments on spider mite populations.

It was also observed that there was a significant reduction in the population of two-spotted spider mite (*Tetranychus urticae*) on the leaves of plants grown from JA-treated seeds compared with populations on control plants (FIG. 2). The control plants were placed at least 10 meters away from any JA treated plants and the illustrated data are means of 10 replicates+/−standard error of the mean.

It was further observed that there was a significant reduction in the reproductive rate of the mite measured by egg production (FIG. 3), compared with control plants. The control plants were placed at least 10 meters away from any JA treated plants and the illustrated data are means of 10 replicates+/−standard error of the mean.

FIG. 2. shows the effects of JA seed treatments on spider mite populations, in which the legends are as follows:
X2=JA concentration in seed treatment (mM); and
Y2=Number of live mites.

Figure 3:
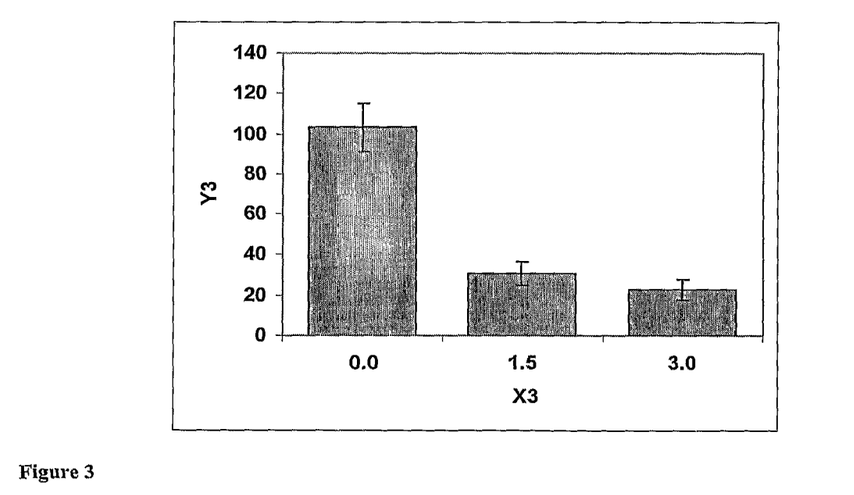
FIG. 3. shows the effects of JA seed treatments on egg production by spider mite populations.

FIG. 3. shows the effects of JA seed treatments on egg production by spider mite populations, in which the legends are as follows:
X3=JA concentration in seed treatment (mM); and
Y3=Eggs produced per adult female.

EXAMPLE 2

Figure 4:
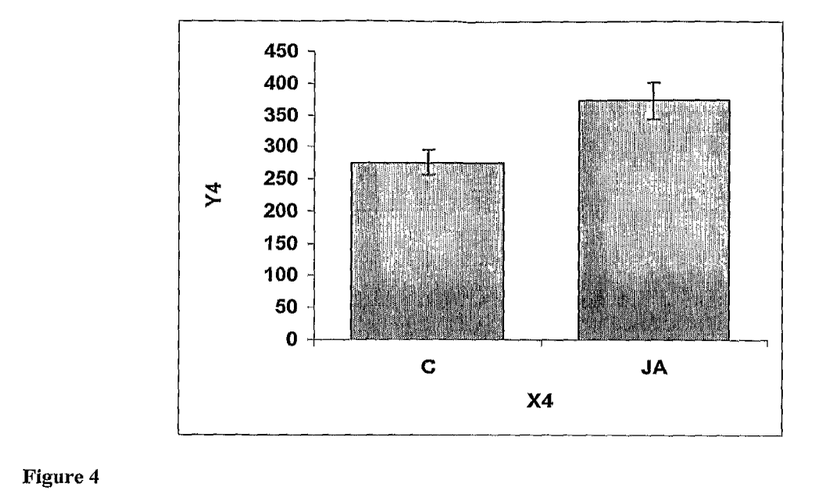
FIG. 4. shows the effects of JA seed treatments on grazing by *Manduca sexta* caterpillars.

Seeds of a UK commercial F1 hybrid tomato variety (cv. Carousel) were treated with 1.5 mM jasmonic acid (JA), and plants grown in conditions appropriate to this crop (as described under Example 1). Eight weeks after seed treatment, plants grown from treated seed were challenged with a leaf chewing herbivore by placing two third instar caterpillars of the moth *Manduca sexta* (tobacco hornworm) on the fifth leaf. Caterpillars were allowed to feed on the plants for four days and the area of grazed leaves was then measured. The leaf area remaining after grazing was significantly higher in plants grown from seed treated with JA than controls (FIG. 4). In addition, caterpillars grazing on leaves of plants grown from seed treated with JA grew 20% less than those feeding on controls. Control seeds were treated with the appropriate ethanol solution but were kept close to plants grown from JA treated seed. The illustrated data are means of 10 replicates+/−standard error of the mean.

FIG. 4. shows the effects of JA seed treatments on grazing by *Manduca sexta* caterpillars, in which the legends are as follows:

X4=Seed treatment with C=Control and JA=Jasmonic acid treated; and

Y4=Leaf area after grazing (cm$^2$).

EXAMPLE 3

Figure 5:
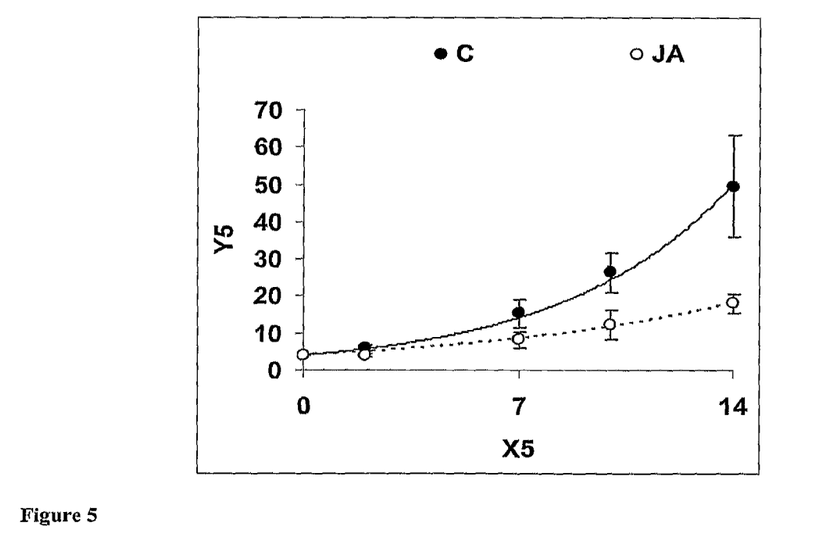
FIG. 5. shows the effects of JA seed treatments on *Myzus persicae* populations in sweet pepper (*Capsicum annuum*)

In experiments in which seeds of sweet pepper (*Capsicum annuum*, cv Biscayne) were treated with 1.5 mM jasmonic acid (JA), and plants grown in conditions appropriate to this crop (as described under the Overview). Eight weeks after seed treatment, plants grown from treated seed were challenged with the aphid *Myzus persicae*. Aphids were allowed to feed on the plants for two weeks and the growth of the aphid population over this period was then measured. There was a significant ($p<0.001$) reduction in the rate of aphid population growth on plants grown from seed treated with JA (FIG. 5). Control seeds were treated with the appropriate ethanol solution but were kept close to plants grown from JA treated seed. The illustrated data are means of 10 replicates+/−standard error of the mean, and the lines are fitted growth curves, which give population growth rates of 0.19+/−0.011 for controls and 0.11+/−0.016 for JA treated.

FIG. 5. shows the effects of JA seed treatments on *Myzus persicae* populations in sweet pepper (*Capsicum annuum*), in which the legends are as follows:

X5=Days after introducing aphids; and

Y5=Number of aphids with C=Control and JA=Jasmonic acid treated.

EXAMPLE 4

Figure 6:
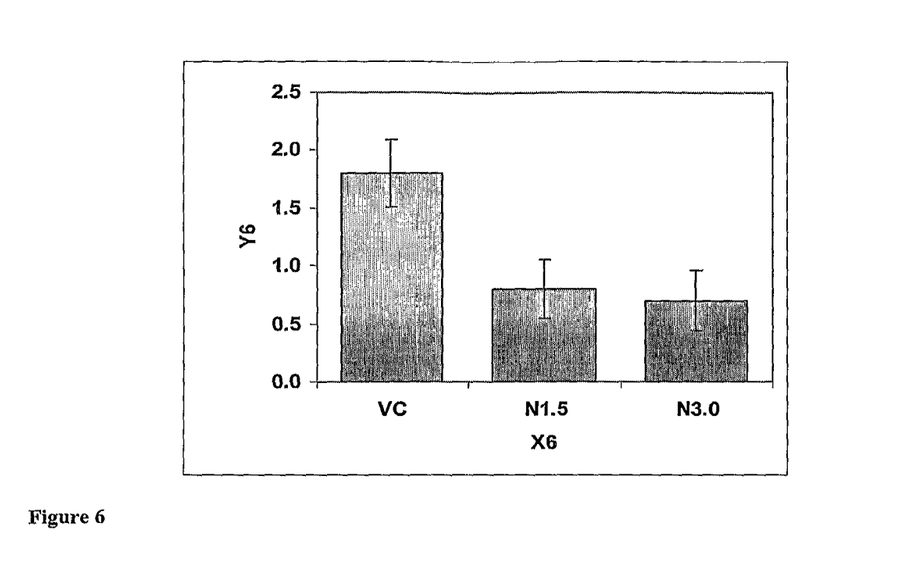
FIG. 6. shows the effects of JA seed treatments on spider mite populations in nearby untreated plants.

In experiments in which plants of tomato (cv Carousel) were grown under the same conditions and exposed to the same challenge by two-spotted spider mite (*Tetranychus urticae*) as described under Example 1, there was significant reduction in the population of *T. urticae* on plants which had received no JA treatment but had been grown adjacent to plants grown from seeds treated with either 1.5 or 3.0 mM Jasmonic acid (JA). The effect was observed on comparing the controls located at least 10 meters away. (FIG. 6). The illustrated data are means of 10 replicates+/−standard error of the mean.

Figure 7:
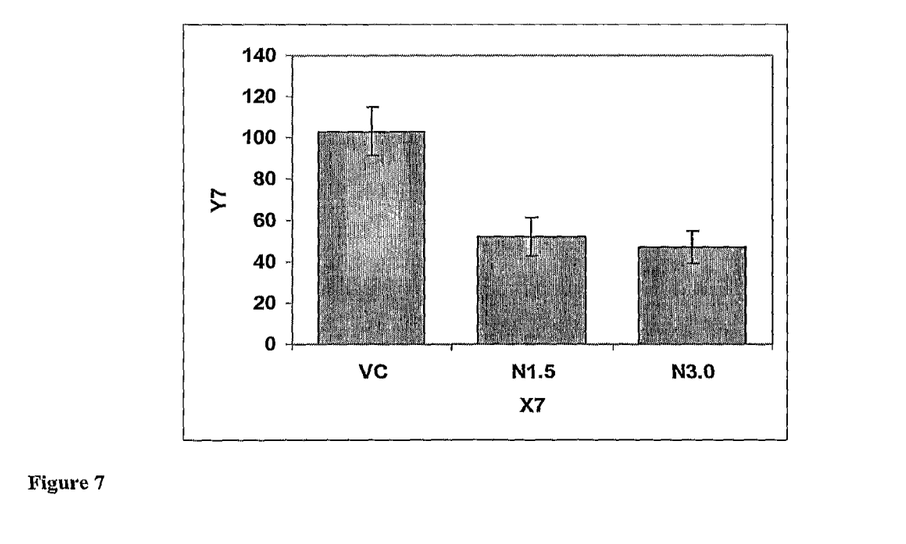
FIG. 7. shows the effects of JA seed treatments on spider mite reproduction in nearby untreated plants.

It was also observed that there was a significant reduction in the reproductive rate of the mite (measured by egg production) on plants which had received no JA treatment but had been grown adjacent to plants grown from seeds treated with either 1.5 or 3.0 mM Jasmonic acid (JA). The effect was again observed on comparing the controls located at least 10 meters away. (FIG. 7). The illustrated data are means of 10 replicates+/−standard error of the mean.

FIG. 6. shows the effects of JA seed treatments on spider mite populations in nearby untreated plants, in which the legends are as follows:

X6=Treatment, with VC=virgin control, N1.5=neighbour of 1.5 mM seed treatment and N3.0=neighbour of 3.0 mM seed treatment; and Y6=Number of live mites.

FIG. 7. shows the effects of JA seed treatments on spider mite reproduction in nearby untreated plants, in which the legends are as follows:

X7=Treatment, with VC=virgin control, N1.5=neighbour of 1.5 mM seed treatment and N3.0=neighbour of 3.0 mM seed treatment; and Y7=Eggs produced per adult female.

EXAMPLE 5

Figure 8:
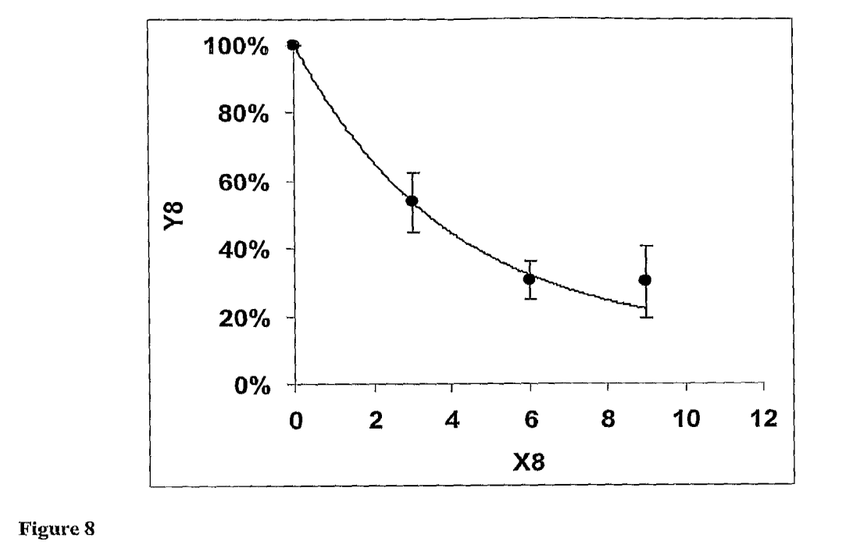
FIG. 8. shows the effects of JA seed treatments on *Myzus persicae* populations in tomato (*Solanum lycopersicum* cv "Carousel")

Seeds of a UK commercial F1 hybrid tomato variety (cv. Carousel) were treated with 3.0 mM jasmonic acid (JA) and 42.8 mM ethanol in deionised $H_2O$ for a period of 24 hours at 4° C. in the dark. Those seeds were then removed from solution and washed in deionised $H_2O$ only to remove the JA coating the outside of the seed, and plants grown in conditions appropriate to this crop (as described under the Overview). Ten weeks after sowing, plants were challenged with the aphid *Myzus persicae*. Aphids were allowed to feed on the plants for twelve days and the aphid population compared with control plants. There was a significant ($p<0.05$) reduction in the aphid population on plants grown from seed treated with JA (FIG. 8). Control seeds were treated with the appropriate ethanol solution but were kept close to plants grown from JA treated seed. The illustrated data are means of 15 replicates+/−standard error of the mean.

FIG. 8. shows the effects of JA seed treatments on *Myzus persicae* populations in tomato (Solanum lycopersicum cv "Carousel"), in which the legends are as follows:

X8=Days after first aphid attack; and

Y8=Number of aphids (treated as % of control).

EXAMPLE 6

Seeds of maize cv. Earligold were treated with 1.5 mM jasmonic acid (JA), and plants grown in the glasshouse (as described under Example 1). At the tassel stage (approx. 10 weeks after seed treatment), plants were challenged with a leaf chewing herbivore by placing two caterpillars of the moth *Spodoptera exempta* on a fully expanded leaf. Caterpillars were allowed to feed on the plants for 2 days and the area of grazed leaves was then measured. The leaf area consumed by caterpillars was 38% lower in plants grown from seed treated with JA than controls (significant at $p<0.05$). When expressed as the area of leaf consumed per unit weight of caterpillars the reduction in plants grown from seed treated with JA was even more pronounced (40%, $p<0.001$, FIG. 9). Control seeds were treated with the appropriate ethanol solution but were kept close to plants grown from JA treated seed. The illustrated data are means of 12 replicates+/−standard error of the mean.

Figure 9:
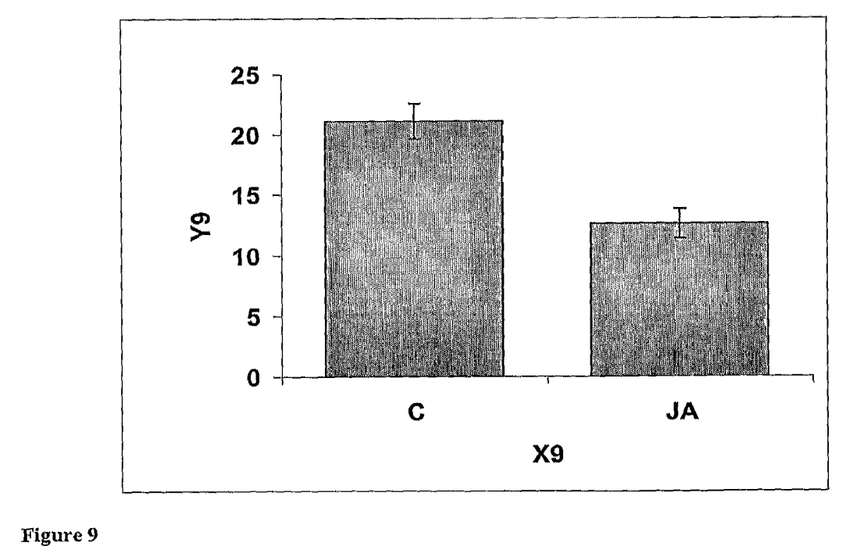
FIG. 9. shows the effects of JA seed treatments on grazing by *Spodoptera exempta* caterpillars on maize.

FIG. 9. shows the effects of JA seed treatments on grazing by *Spodoptera exempta* caterpillars on maize, in which the legends are as follows:

X9=Treatment, with C=Control and JA=Jasmonic acid treated; and

Y9=Leaf area consumed per g caterpillar fresh weight.

EXAMPLE 7

Seeds of the commercial wheat variety (cv. Einstein) were treated with 1.5 mM jasmonic acid (JA), and plants grown in the glasshouse (as described under Example 1). 7 weeks after seed treatment, plants were challenged with a leaf chewing herbivore by placing two caterpillars of the moth *Spodoptera exempta* on each plant. Caterpillars were allowed to feed on the plants for 3 days and the area of grazed leaves was then measured. The leaf area consumed by caterpillars was 60% lower in plants grown from seed treated with JA than controls (significant at $p<0.01$, FIG. 10). Control seeds were treated with the appropriate ethanol solution but were kept close to plants grown from JA treated seed. The illustrated data are means of 10 replicates+/−standard error of the mean.

Figure 10:
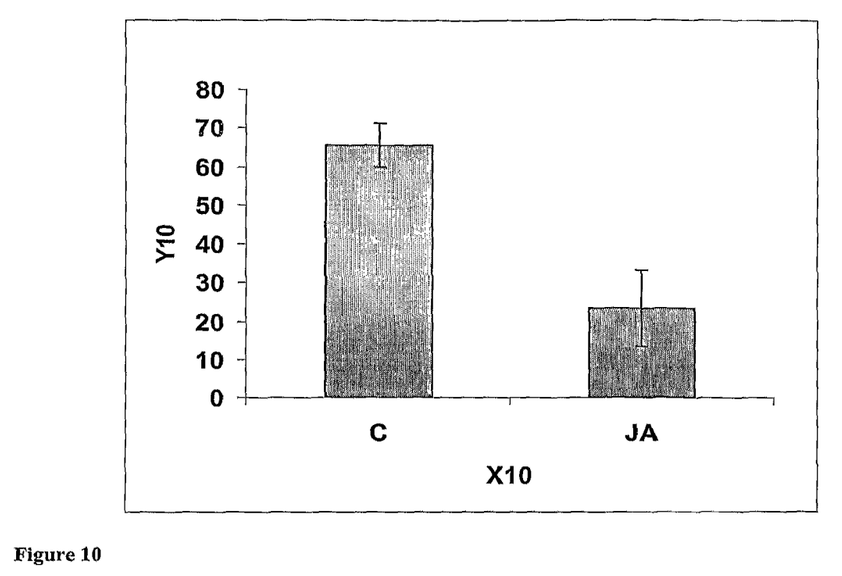
FIG. 10. shows the effects of JA seed treatments' on grazing by *Spodoptera exempta* caterpillars on wheat.

FIG. 10. shows the effects of JA seed treatments on grazing by *Spodoptera exempta* caterpillars on wheat, in which the legends are as follows:
X10=Treatment, with C=Control and JA=Jasmonic acid treatment; and
Y10=Leaf area eaten (cm$^2$).

EXAMPLE 8

Figure 11:
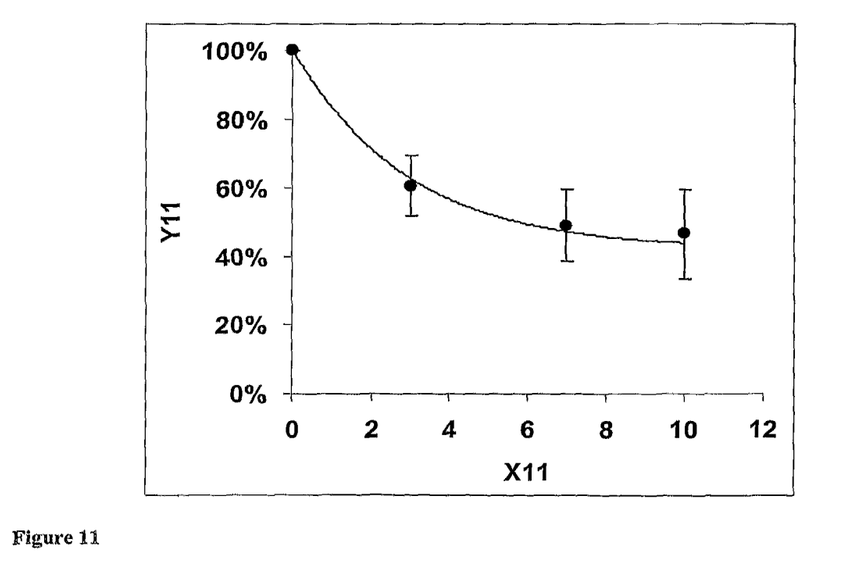
FIG. 11. shows the effects of JA seed treatments on *Myzus persicae* populations in tomato (*Solanum lycopersicum* cv "Carousel") when treated seed was sown after two months storage.

Seeds of a UK commercial F1 hybrid tomato variety (cv. Carousel) were treated with 3.0 mM jasmonic acid (JA) and 42.8 mM ethanol in deionised $H_2O$ for a period of 24 hours at 4° C. in the dark. As in previous examples, those seeds were then removed from solution and washed in deionised $H_2O$ only to remove the JA coating the outside of the seed, but unlike previous examples the treated seed were then dried and stored dry in a refrigerator at 4° C. for two months before sowing. After sowing plants were grown in conditions appropriate to this crop (as described under the Overview). Ten weeks after sowing, plants were challenged with the aphid *Myzus persicae*. Aphids were allowed to feed on the plants for ten days and the aphid population compared with control plants. There was a significant ($p<0.05$) reduction in the aphid population on plants grown from seed treated with JA (FIG. 11). Control seeds were treated with the appropriate ethanol solution but were kept close to plants grown from JA treated seed. The illustrated data are means of 15 replicates+/−standard error of the mean.

FIG. 11. shows the effects of JA seed treatments on *Myzus persicae* populations in tomato (*Solanum lycopersicum* cv "Carousel") when treated seed was sown after two months storage, in which the legends are as follows:
X11=Days after first aphid attack; and
Y11=Number of aphids (treated as % of control).

EXAMPLE 9

Figure 12:
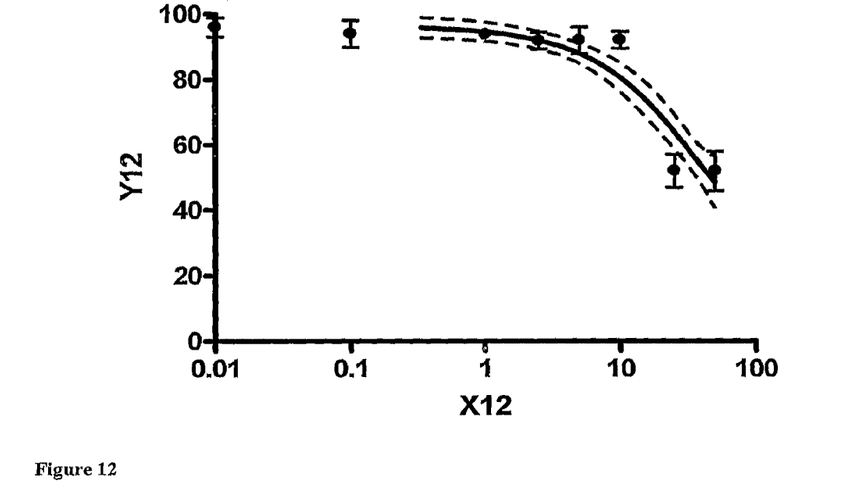
FIG. 12. shows the effects of JA seed treatments on seed germination of tomato (*Solanum lycopersicum* cv "Carousel") 7 days after sowing.

Germination of seeds of a UK commercial F1 hybrid tomato variety (cv. Carousel) was delayed by approximately one day when seeds were treated with either 1.5 or 3.0 mM jasmonic acid (JA) and 42.8 mM ethanol in deionised $H_2O$ for a period of 24 hours at 4° C. in the dark. These treatments had no significant effects on the final percentage germination. When seeds were treated with a wider range of concentrations of jasmonic acid (JA) between 0.001 and 50 mM under the same conditions, the final percentage germination was significantly reduced only by concentrations in excess of 10 mM (FIG. 12). The illustrated data are means of 10 replicate populations+/−standard error of the mean, and the line is a fitted dose response.

FIG. 12. shows the effects of JA seed treatments on seed germination of tomato (Solanum lycopersicum cv "Carousel") 7 days after sowing, in which the legends are as follows:
X12=JA concentration (mM log scale); and
Y12=Seed germination (%) after 7 days.

EXAMPLE 10

In long term studies of growth and yield where plants were harvested at weekly intervals, seed treatment with 1.5 or 3.0 mM JA, as in Example 9, there was no significant effect on the vegetative or reproductive growth, or commercial yield of tomato, cucumber or pepper. For example, the illustrated data for tomato (cv. Carousel) show no significant effects on plant height (FIG. 13), number of fruit (FIG. 14) or fruit dry weight (FIG. 15) at each weekly harvest. Data are means of 8 replicate plants+/−standard error of the mean, and the line is a fitted growth response. Neither the fitted growth response nor 2-way analysis of variance (treatment×harvest) showed any significant difference between control plants and those grown from JA-treated seed.

Figure 13:
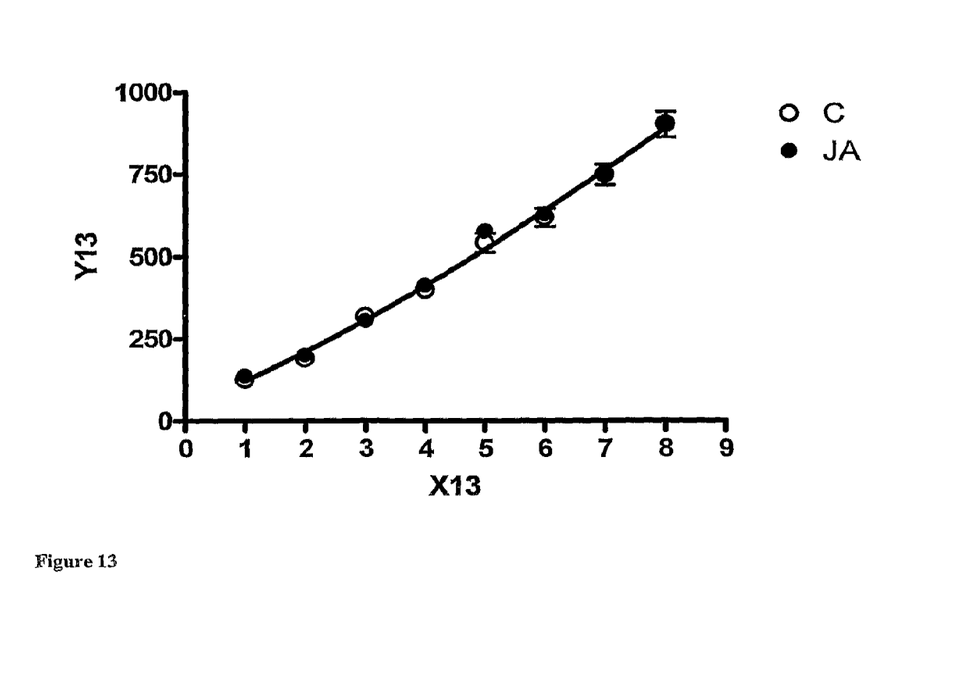
FIG. 13. shows the effects of JA seed treatments on plant height of tomato (*Solanum lycopersicum* cv "Carousel") at weekly harvests.

FIG. 13. shows the effects of JA seed treatments on plant height of tomato (Solanum lycopersicum cv "Carousel") at each weekly harvest, in which the legends are as follows:
X13=Harvest (weeks); and
Y13=Plant height (cm) with C=Control and JA=Jasmonic acid treatment.

Figure 14:
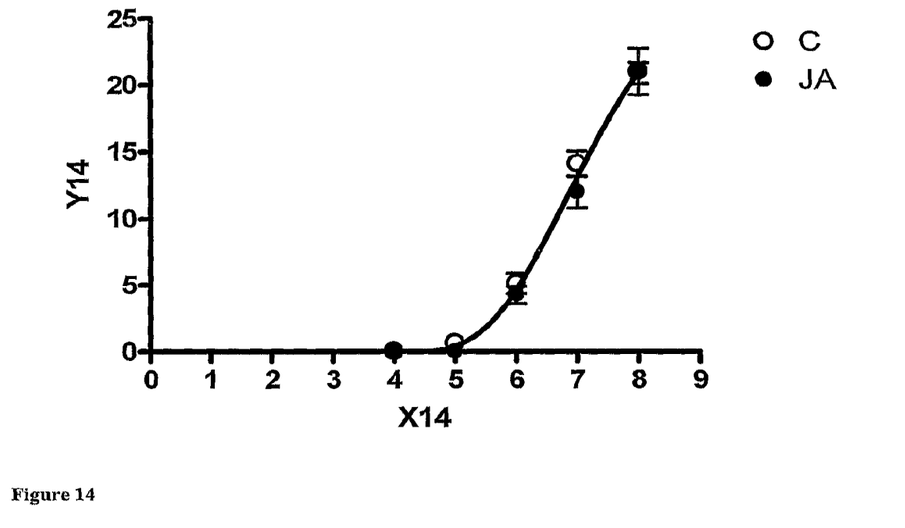
FIG. 14. shows the effects of JA seed treatments on number of fruit per plant of tomato (*Solanum lycopersicum* cv "Carousel") at weekly harvests.

FIG. 14. shows the effects of JA seed treatments on number of fruit per plant of tomato (Solanum lycopersicum cv "Carousel") at each weekly harvest, in which the legends are as follows:
X14=Harvest (weeks); and
Y14=Number of fruit with C=Control and JA=Jasmonic acid treatment.

Figure 15:
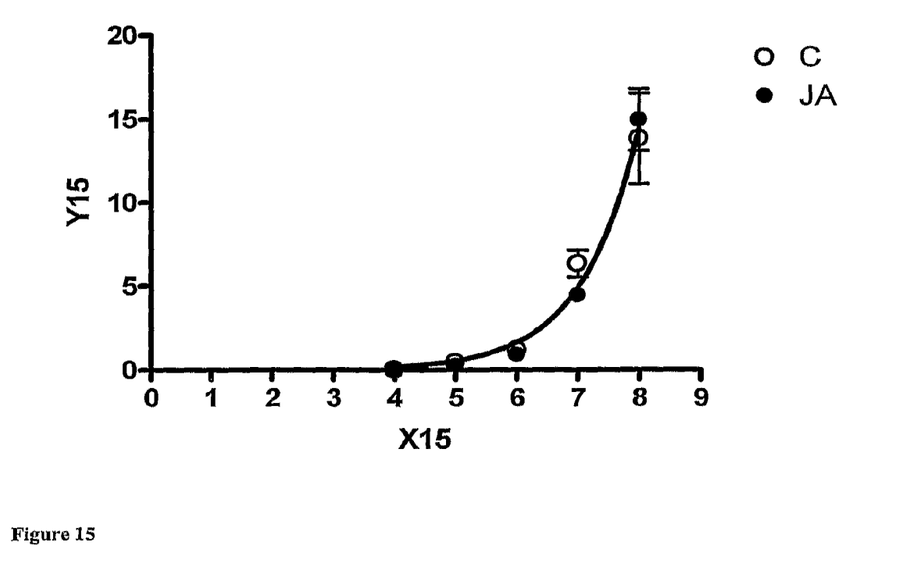
FIG. 15. shows the effects of JA seed treatments on fruit dry weight from tomato (*Solanum lycopersicum* cv "Carousel") at weekly harvests.

FIG. 15. shows the effects of JA seed treatments on fruit dry weight from tomato (Solanum lycopersicum cv "Carousel") at each weekly harvest, in which the legends are as follows:
X15=Harvest (weeks); and
Y15=Fruit dry weight (g) with C=Control and JA=Jasmonic acid treatment.

EXAMPLE 11

Seeds of a UK commercial F1 hybrid tomato variety (cv. Carousel) were treated with 3.0 mM methyl jasmonate (MeJA) and 42.8 mM ethanol in deionised $H_2O$ for a period of 24 hours at 4° C. in the dark. Those seeds were then removed from solution and washed in deionised $H_2O$ only to remove the MeJA coating the outside of the seed, and plants grown in conditions appropriate to this crop (as described under the Overview). Ten weeks after seed treatment, plants grown from treated seed were challenged with the aphid *Myzus persicae*. Aphids were allowed to feed on the plants for twelve days and the aphid population was measured at intervals over this period. Compared with control plants, there was a significant ($p<0.05$) reduction in the aphid population on plants grown from seed treated with MeJA (FIG. 16) Control seeds were treated with the appropriate ethanol solution but were kept close to plants grown from JA treated seed. The illustrated data are means of 12 replicates+/−standard error of the mean.

Figure 16:
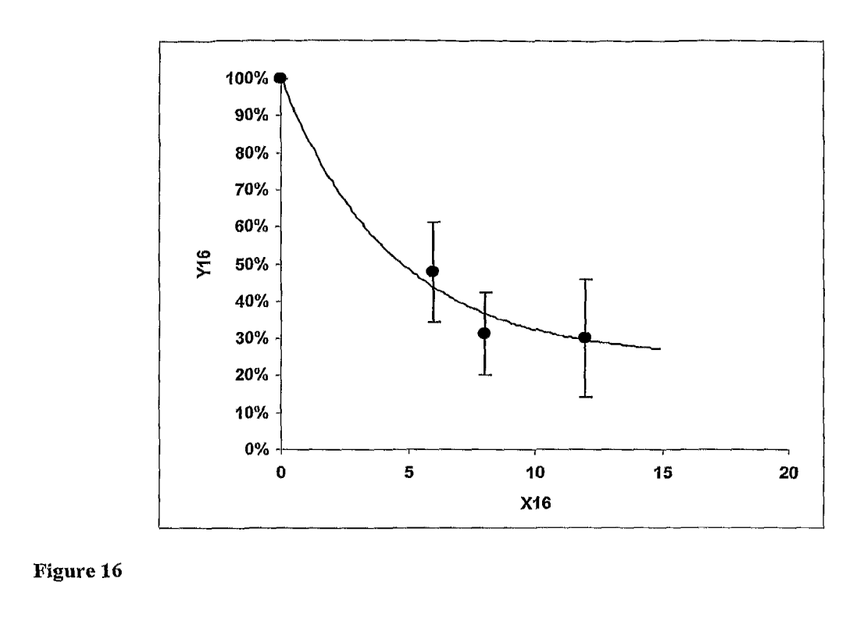
FIG. 16. shows the effects of MeJA seed treatments on *Myzus persicae* populations in tomato (*Solanum lycopersicum* cv "Carousel")

FIG. 16. shows the effects of MeJA seed treatments on *Myzus persicae* populations in tomato (*Solanum lycopersicum* cv. "Carousel"), in which the legends are as follows:
X16=Days after challenge with aphids; and
Y16=Aphid number (treated as % of control).

EXAMPLES SUMMARY

From Examples 1 to 11, tomato, sweet pepper, maize and wheat plants grown from treated seed were observed to be protected against insect and other pests when challenged up to 10 weeks after sowing (Table 1).

TABLE 1

| Crop | Pest | Weeks from sowing | Treatment | Example |
|---|---|---|---|---|
| Tomato | *Tetranychus urticae* | 7 | Jasmonic acid 1.5 & 3 mM | 1 |
| Tomato | *Menduca sexta* | 8 | Jasmonic acid 1.5 mM | 2 |
| Tomato | *Myzus persicae* | 10 | Jasmonic acid 3 mM | 5 & 8 |
| Tomato | *Myzus persicae* | 10 | Methyl jasmonate 3 mM | 11 |
| Sweet Pepper | *Myzus persicae* | 8 | Jasmonic acid 1.5 mM | 3 |
| Maize | *Spodotera exempta* | 10 | Jasmonic acid 1.5 mM | 6 |
| Wheat | *Spodotera exempta* | 7 | Jasmonic acid 1.5 mM | 7 |

Table 1 shows the tested time periods after which tomato (*Solanum lycopersicum* cv "Carousel"), sweet pepper (*Capsicum annuum*, cv Biscayne), maize (cv. Earligold) and wheat (cv. Einstein) plants grown from seed treated with jasmonic acid or methyl jasmonate were challenged with various pests and found to exhibit pest resistance.

It will be appreciated that preferred embodiments of the methods, seeds, plants and compositions of the invention may have significant benefits. By applying a treatment composition comprising a plant signalling chemical (treatment agent) to a seed to induce the natural resistance mechanisms of the plant, for example those acting against pests so as to reduce the survival, feeding or reproduction of pests, crop damage may be reduced. By applying such a composition prior to germination it may be possible to then prime subsequent seedlings and mature plants against pest attack in a surprisingly expedient and effective manner. Given the mode of action of the treatment composition it is believed preferred embodiments may have a major role within IPM approaches and/or in reducing levels of use of pesticides.

Preferred embodiments of methods and compositions for treating seeds may provide effective protection to subsequent plants against herbivorous arthropods and other pests. Such protection may be effective over an extended time period. Surprisingly, treatment of non-germinating seed may be effective which may allow the seed to be stored for significant periods between treatment and sowing. Beneficially problems of phytotoxicity may be avoided.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A seed from which a plant resistant to pest damage can be grown, wherein the seed comprises a seed treated with a seed treatment composition to induce a plant resistance mechanism against one or more pests in a plant grown from said seed so as to restrict plant damage by pests, the treatment composition comprising a treatment agent selected from jasmonic acid (JA) or related members of the jasmonate family of oxylipins, or other compounds that activate JA-dependant herbivore resistance pathways including: jasmonic acid or its jasmonate salts, such as, for example, potassium or sodium jasmonate; jasmonic acid methyl ester ('methyl jasmonate'); jasmonic acid-L-amino acid (amide-linked) conjugates, such as, for example, the conjugate with Lisoleucine or the conjugates with L-valine, L-leucine and L-phenylalanine; 12-oxo-phytodienoic acid; coronatine (an amide of coronafacic acid with 2-ethyl-1-aminocyclopropane carboxylic acid); coronafacoyl-L-serine and coronafacoyl-L-threonine; methyl esters of 1-oxo-indanoylisoleucine and 1-oxo-indanoyl-leucine; coronalon (2-[(6-ethyl-1-oxo-indane-4-carbonyl)-amino]3-methyl-pentanoic acid methyl ester); or combinations thereof.

2. The seed of claim 1, wherein the treatment composition comprises jasmine acid (JA) or methyl jasmonate (MeJA).

3. The seed of claim 1, wherein the seed is a non-germinated seed.

4. The seed of claim 1, wherein the pests comprise herbivorous invertebrates.

5. The seed of claim 1, wherein the treatment composition comprises water, the treatment agent and an alcohol.

* * * * *